United States Patent
Hutton et al.

(10) Patent No.: US 8,927,706 B2
(45) Date of Patent: Jan. 6, 2015

(54) BASED-ASSISTED FORMATION OF TIN-SUCROSE ADDUCTS

(75) Inventors: Thomas Kennedy Hutton, Lafayette, IN (US); Peter Jay Seaberg, Decatur, IL (US); Christopher C. Kerwood, Lafayette, IN (US)

(73) Assignee: Tate & Lyle Technology, Ltd., London (GB)

( * ) Notice: Subject to any disclaimer, the term of this patent is extended or adjusted under 35 U.S.C. 154(b) by 229 days.

(21) Appl. No.: 13/262,102

(22) PCT Filed: Mar. 10, 2010

(86) PCT No.: PCT/US2010/026784
§ 371 (c)(1),
(2), (4) Date: Dec. 27, 2011

(87) PCT Pub. No.: WO2010/114683
PCT Pub. Date: Oct. 7, 2010

(65) Prior Publication Data
US 2012/0095199 A1    Apr. 19, 2012

Related U.S. Application Data

(60) Provisional application No. 61/165,162, filed on Mar. 31, 2009.

(51) Int. Cl.
| | | |
|---|---|---|
| C07H 1/00 | (2006.01) |
| C07H 3/04 | (2006.01) |
| C07H 5/02 | (2006.01) |
| A23L 1/236 | (2006.01) |
| C07H 13/04 | (2006.01) |
| C07H 23/00 | (2006.01) |

(52) U.S. Cl.
CPC .. *C07H 1/00* (2013.01); *C07H 3/04* (2013.01); *C07H 5/02* (2013.01); *A23L 1/236* (2013.01); *C07H 13/04* (2013.01); *C07H 23/00* (2013.01)
USPC ....................................................... 536/123

(58) Field of Classification Search
None
See application file for complete search history.

(56) References Cited

U.S. PATENT DOCUMENTS

| | | |
|---|---|---|
| 4,783,526 A | 11/1988 | O'Brien et al. |
| 4,889,928 A | 12/1989 | Simpson |
| 4,950,746 A | 8/1990 | Navia |
| 4,980,463 A | 12/1990 | Walkup et al. |
| 5,023,329 A | 6/1991 | Neiditch et al. |
| 5,034,551 A | 7/1991 | Vernon et al. |
| 5,089,608 A | 2/1992 | Walkup et al. |
| 5,270,071 A | 12/1993 | Sharp et al. |
| 5,272,137 A | 12/1993 | Blase et al. |
| 5,298,611 A | 3/1994 | Navia et al. |
| 5,354,902 A | 10/1994 | Merciadez et al. |
| 5,374,659 A | 12/1994 | Gowan |
| 5,384,311 A | 1/1995 | Antenucci et al. |
| 5,397,588 A | 3/1995 | Antenucci et al. |
| 5,409,907 A | 4/1995 | Blase et al. |
| 5,440,026 A | 8/1995 | Kahn et al. |
| 5,470,969 A | 11/1995 | Sankey et al. |
| 5,498,709 A | 3/1996 | Navia et al. |
| 5,593,696 A | 1/1997 | McNally et al. |
| 5,621,005 A | 4/1997 | Gowan |
| 5,658,919 A | 8/1997 | Ratnaraj et al. |
| 5,674,522 A | 10/1997 | Shah et al. |
| 5,817,340 A | 10/1998 | Roche et al. |
| 5,876,759 A | 3/1999 | Gowan |
| 5,977,349 A | 11/1999 | Catani et al. |
| 6,080,481 A | 6/2000 | Ochs et al. |
| 6,090,401 A | 7/2000 | Gowan et al. |
| 6,211,246 B1 | 4/2001 | Gelotte et al. |
| 6,258,381 B1 | 7/2001 | Luber et al. |
| 6,265,012 B1 | 7/2001 | Shamil |
| 6,277,409 B1 | 8/2001 | Luber et al. |
| 6,646,121 B2 | 11/2003 | El Kabbani et al. |
| 6,809,198 B2 | 10/2004 | El Kabbani et al. |
| 6,890,581 B2 | 5/2005 | Vernon et al. |
| 6,939,962 B2 | 9/2005 | Clark et al. |
| 6,943,248 B2 | 9/2005 | Catani et al. |
| 6,998,144 B2 | 2/2006 | Merkel et al. |
| 6,998,480 B2 | 2/2006 | Catani et al. |
| 7,049,435 B2 | 5/2006 | Catani et al. |
| 2004/0030124 A1 | 2/2004 | Catani et al. |
| 2006/0188629 A1 | 8/2006 | Liesen et al. |
| 2006/0205936 A1 | 9/2006 | Jia et al. |
| 2006/0276639 A1 | 12/2006 | Fry |
| 2007/0015916 A1 | 1/2007 | El Kabbani et al. |
| 2007/0100139 A1 | 5/2007 | Fry |

(Continued)

FOREIGN PATENT DOCUMENTS

| | | |
|---|---|---|
| EP | 0 448 413 A1 | 9/1991 |
| EP | 0 475 619 A1 | 3/1992 |

(Continued)

OTHER PUBLICATIONS

Iwasaki et al. Chemo- and Stereoselective Monobenzoylation of 1,2-Diols Catalyzed by Organotin Compounds. J. Org. Chem. 2000, 65, 996-1002.*

(Continued)

*Primary Examiner* — Eric Olson
*Assistant Examiner* — Dale R Miller
(74) *Attorney, Agent, or Firm* — RatnerPrestia

(57) ABSTRACT

A method of forming a sucrose-6-ester includes in sequence the steps of: a) contacting sucrose with a organotin-based acylation promoter in a solvent in the presence of a base selected from amines and basic alkali metal salts; b) removing water to form a tin-sucrose adduct; and c) contacting the tin-sucrose adduct with an acylating agent to form the sucrose-6-ester. The sucrose-6-ester may then be converted to sucralose.

17 Claims, No Drawings

(56) References Cited

U.S. PATENT DOCUMENTS

| | | | |
|---|---|---|---|
| 2007/0160732 A1 | 7/2007 | Deshpande et al. | |
| 2007/0227897 A1 | 10/2007 | Li et al. | |
| 2007/0270583 A1 | 11/2007 | Ratnam et al. | |
| 2009/0076261 A1* | 3/2009 | Xu | 536/127 |

FOREIGN PATENT DOCUMENTS

| | | | | |
|---|---|---|---|---|
| EP | 0 776 903 A1 | 6/1997 | | |
| JP | 2001247592 A * | 9/2001 | | B01J 31/12 |
| WO | WO 2008/084197 A1 | 7/2008 | | |

OTHER PUBLICATIONS

Reich and Rigby, Eds. Acidic and Basic Reagents, John Wiley and Sons, New York, 1999.*

Carraher, Organotin Polymers, Chapter 10, In: Macromolecules Containing Metal and Metal-Like Elements, vol. 4: Group IVA Polymers, edited by Alaa S. Abd-El-Aziz, Charles E. Carraher Jr., Charles U. Pittman Jr., and Martel Zeldin, 2005, John Wiley & Sons, Inc.*

Ishhiro et al., JP 2001247592 A, Sep. 2001, machine translation, Retreived on Jun. 19, 2014 from http://worldwide.espacenet.com.*

Morcuende, A., Valverde, S., & Herradón, B. (1994). Rapid formation of dibutylstannylene acetals from polyhydroxylated compounds under microwave heating. Application to the regioselective protection of polyols and to a catalytic Tin-mediated benzoylation. Synlett, 1994(01), 89-91.*

Mezzato, Stefano, International Search Report dated Apr. 27, 2010.

Lindner, Nora, International Preliminary Report on Patentability dated Oct. 4, 2010.

Yu et al., Kuo-Long, "A Novel Reagent for the Synthesis of Myo-Inositol Phosphates: N,N-Diisopropyl Dibenzyl Phosphoramidite," Tetrahedron Letters, vol. 29, No. 9, pp. 979-982, 1988.

Richards, G.N., "Sucrose Losses in Sugar and Food Processing—Effects of Impurities," Proceedings of the 1988 Sugar Processing Research Conference, pp. 115-129, Oct. 1989.

Evans, Stephen, Combined Search and Examination Report under Sections 17 and 18(3) dated Feb. 23, 2010.

* cited by examiner

BASED-ASSISTED FORMATION OF TIN-SUCROSE ADDUCTS

CROSS REFERENCE TO RELATED APPLICATIONS

This application is the national phase filing of international patent application No. PCT/US2010/026784, filed 10 Mar. 2010, and claims priority of U.S. Appln. No. 61/165,162, filed 31 Mar. 2009, the entireties of which applications are incorporated herein by reference.

BACKGROUND OF THE INVENTION

Sucralose (4,1',6'-trichloro-4,1',6'-trideoxygalactosucrose), a high-intensity sweetener made from sucrose, can be used in many food and beverage applications.

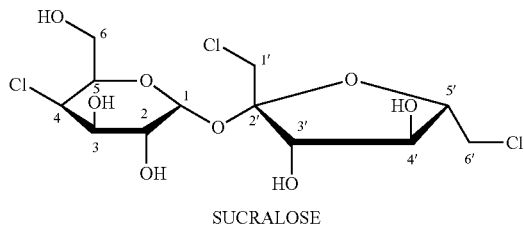

SUCRALOSE

A number of different synthesis routes for the preparation of sucralose have been developed in which the reactive hydroxyl in the 6 position is first blocked with an acyl group to form a sucrose-6-ester. The acyl group is typically acetyl or benzoyl, although others may be used. The sucrose-6-ester is then chlorinated to replace the hydroxyls at the 4, 1' and 6' positions to produce 4,1',6'-trichloro-4,1',6'-trideoxygalactosucrose 6-ester (referred to herein as sucralose-6-ester), followed by hydrolysis to remove the acyl substituent and thereby produce sucralose. Several synthesis routes for formation of the sucrose-6-ester involve tin-mediated acylation reactions, with illustrative examples being disclosed in U.S. Pat. Nos. 4,950,746; 5,023,329; 5,089,608; 5,034,551; and 5,470,969, all of which are incorporated herein by reference.

Various chlorinating agents may be used to chlorinate the sucrose-6-ester, and most commonly a Vilsmeier-type salt such as Arnold's Reagent will be used. One suitable chlorination process is disclosed by Walkup et al. (U.S. Pat. No. 4,980,463), incorporated herein by reference. This process uses a tertiary amide, typically N,N-dimethyl formamide ("DMF"), as the chlorination reaction solvent. After the chlorination is complete, adducts of Arnold's reagent on the base sucrose moiety and excess chlorinating reagent are neutralized ("quenched") with aqueous base to provide the sucralose-6-ester in an aqueous solution, accompanied by the tertiary amide solvent and salts resulting from reactions of the chlorination reagent. The sucralose-6-ester is then deacylated to produce sucralose. One suitable deacylation process is taught by Navia et al, U.S. Pat. No. 5,498,709, the entire disclosure of which is incorporated herein by reference. It will be apparent that improving the yield and selectivity of sucrose-6-ester preparation would increase sucralose yield and process efficiency, as well as simplify purification.

SUMMARY OF THE INVENTION

The invention provides a method of forming a sucrose-6-ester. The method includes, in sequence, the steps of:

a) contacting sucrose with a organotin-based acylation promoter in a solvent in the presence of a base selected from amines and basic alkali metal salts;
b) removing water to form a tin-sucrose adduct; and
c) contacting the tin-sucrose adduct with an acylating agent to form the sucrose-6-ester.

DETAILED DESCRIPTION OF THE INVENTION

The invention provides methods of producing sucralose in which, during formation of an intermediate sucrose-6-ester, a base is included with a mixture of sucrose and an organotin-based acylation promoter prior to the water removal ("dehydration") step which forms a tin-sucrose adduct that is subsequently acylated to form the ester. The addition of base at this point in the process may increase the yield and selectivity of the tin-mediated acylation of sucrose to produce the sucrose-6-ester. An overall process for producing sucralose according to the invention will now be described, followed by more detailed disclosure of the various steps.

One suitable process for the preparation of sucralose from sucrose involves the following steps. First, the hydroxyl in the 6 position of sucrose is blocked with an ester group, such as acetate or benzoate. Then the hydroxyls in the 4, 1', and 6' positions of the resulting sucrose-6-ester are converted to chloro groups, with inversion of the stereochemical configuration at the 4 position. Conversion of the hydroxyls in the 4, 1', and 6' positions of the ester to chloro groups with inversion of the stereochemical configuration at the 4 position is disclosed in Walkup, U.S. Pat. No. 4,980,463; Jai, U.S. Pat. Pub. 2006/0205936 A1; and Fry, U.S. Pat. Pub. 2007/0100139 A1; the disclosures of which are all incorporated herein by reference. Then the ester group in the 6 position of the resulting sucralose-6-ester is removed, and sucralose, the resulting product, is purified and isolated. The process, or any of the individual steps thereof, can be either batch or continuous processes. Following are details of how some embodiments of the process may be performed.

Preparation of Sucrose-6-Ester

Selective protection of the 6-hydroxyl of sucrose can be carried out by reaction of sucrose with a carboxylic acid anhydride, such as acetic anhydride or benzoic anhydride, in an anhydrous polar aprotic solvent in the presence of an organotin-based acylation promoter, at a temperature and for a period of time sufficient to produce the sucrose-6-ester. The 6-ester group shields the hydroxyl on the 6 position from the chlorination reaction. Accordingly, any ester group that is stable to the conditions of the chlorination reaction and which can be removed under conditions that do not affect the resulting sucralose can be used. When sucrose-6-acetate is prepared, 1,3-diacetoxy-1,1,3,3-tetrabutyldistannoxane, for example, can be used as the organotin-based acylation promoter and acetic anhydride as the carboxylic acid anhydride. Preparation of sucrose-6-esters is disclosed in, for example, O'Brien, U.S. Pat. No. 4,783,526; Navia, U.S. Pat. No. 4,950,746; Simpson, U.S. Pat. No. 4,889,928; Neiditch, U.S. Pat. No. 5,023,329; Walkup, U.S. Pat. No. 5,089,608; Vernon, U.S. Pat. No. 5,034,551; Sankey, U.S. Pat. No. 5,470,969; Kahn, U.S. Pat. No. 5,440,026; Clark, U.S. Pat. No. 6,939,962, and Li, U.S. Pat. Pub. 2007/0227897 A1; the disclosures of which are all incorporated herein by reference.

A typical preparation of sucrose-6-ester employs a two-step process. First, sucrose is contacted in a solvent with an organotin-based acylation promoter and water of reaction is removed to form a tin-sucrose adduct. Then, the reaction mixture containing the tin-sucrose adduct is contacted with a carboxylic acid anhydride. The sucrose-6-ester can be isolated from the resulting reaction mixture. Alternatively, the organotin acylation promoter and/or its reaction products can be removed from the reaction mixture, and the resulting solution of the sucrose-6-ester in the polar aprotic solvent used in the next step, conversion of the hydroxyls at the 4, 1', and 6'-positions to chloro groups.

The choice of polar aprotic solvent is determined by the solubility in the solvent of sucrose, the organotin-based acylation promoter, and the resulting stannylated sucrose product, as well as by safety and toxicity considerations. Preferably the boiling point of the polar aprotic solvent is greater than the boiling point of water at atmospheric pressure. More preferably the boiling point of the polar aprotic solvent is at least 50° C. greater than the boiling point of water at atmospheric pressure. Suitable polar aprotic solvents are, for example, N-methyl-2-pyrrolidone, dimethyl sulfoxide, N,N-dimethyl acetamide, hexamethylphosphoramide, and, preferably, N,N-dimethyl formamide.

The amount of the polar aprotic solvent to be used will also be determined by the above-mentioned solubility considerations. When the polar aprotic solvent is N,N-dimethyl formamide, typically about 8 g to about 22 g of polar aprotic solvent per 1 g of sucrose, preferably about 8 g to about 12 g of polar aprotic solvent per 1 g of sucrose, can be used.

The organotin-based acylation promoter can be any of those known in the art, for example, any of those disclosed in Navia, U.S. Pat. No. 4,950,746; Neiditch, U.S. Pat. No. 5,023,329; Walkup, U.S. Pat. No. 5,089,608; and/or Vernon, EP-0 475 619-A, the disclosures of which are all incorporated herein by reference. In particular, the organotin-based acylation promoter can be: a 1,3-di(hydrocarbyloxy)-1,1,3,3-tetra-(hydrocarbyl)distannoxane; a di(hydrocarbyl)tin oxide; the reaction product of a di(hydrocarbyl)tin oxide and a dihydric alcohol, an alkanolamine, or an enolizable α-hydroxyketone; and a 1,3-diacyloxy-1,1,3,3-tetra-(hydrocarbyl)distannoxane. A di(hydrocarbyl)tin dialkoxide (for example, dimethoxide) may also be used. The term "hydrocarbyl" refers to an alkyl, cycloalkyl, aryl, or aralkyl group. The organotin-based acylation promoter is preferably a 1,3-diacyloxy-1,1,3,3-tetra-(hydrocarbyl)distannoxane.

When the organotin-based acylation promoter is a 1,3-di(hydrocarbyloxy)-1,1,3,3-tetra-(hydrocarbyl)distannoxane, the hydrocarbyloxy group is preferably a $C_1$-$C_8$ alkoxy group or phenoxy, more preferably methoxy, ethoxy, n-propyloxy, n-butyloxy, n-pentyloxy or n-hexyloxy, and most preferably a methoxy group. The hydrocarbyl group in turn is preferably an alkyl group, more preferably a $C_1$-$C_8$ alkyl group, and most preferably an n-butyl group.

When the organotin-based acylation promoter is a di(hydrocarbyl)tin oxide, the hydrocarbyl group is preferably an alkyl group, more preferably a $C_1$-$C_8$ alkyl group, and most preferably an n-butyl group.

When the organotin-based acylation promoter is the reaction product of a di(hydrocarbyl)tin oxide and a dihydric alcohol, an alkanolamine, or an enolizable α-hydroxyketone, the di(hydrocarbyl)tin oxide is preferably as described above. The dihydric alcohol can be an alkane diol, preferably having from 2 to 8 carbon atoms. Suitable examples are ethylene glycol, 2,3-propanediol, 2,3-butanediol, 1,3-butanediol, 1,4-butanediol, 1,3-propanediol, 1,2-pentanediol, and 1,2-hexanediol. Alternatively, the dihydric alcohol can be a cycloalkane diol, preferably having from 5 to 8 carbon atoms. Suitable examples are 1,2-cyclohexanediol and 1,2-cyclopentanediol. In each case, the two hydroxyl groups are preferably not more than four carbon atoms distant from each other on the carbon chain to which they are bonded, and preferably they are on adjacent carbon atoms or there is one carbon atom separating the carbon atoms to which the hydroxyl groups are bonded. The alkanolamine is preferably a $C_2$-$C_8$ alkanolamine, and preferably the hydroxyl group and the amino group are not more than four carbon atoms distant from each other on the carbon chain to which they are bonded, and more preferably the hydroxyl group and the amino group are on adjacent carbon atoms or there is only one carbon atom separating the carbon atoms to which the hydroxyl group and the amino group are bonded. Suitable alkanolamines are ethanolamine, 2-amino-1-propanol, and 1-amino-2-propanol. Suitable enolizable α-hydroxyketones are 2-hydroxy-2-phenylacetophenone and 3-hydroxy-2-butanone.

In some embodiments, the organotin-based acylation promoter is a 1,3-diacyloxy-1,1,3,3-tetra-(hydrocarbyl)distannoxane. The hydrocarbyl group of the 1,3-diacyloxy-1,1,3,3-tetra-(hydrocarbyl)distannoxane is preferably an alkyl group, more preferably a $C_1$-$C_8$ alkyl group, and most preferably a butyl group, so that 1,1,3,3-tetrabutyldistannoxanes are particularly preferred. It is convenient if the acyloxy group matches that of the carboxylic anhydride to be used, so that, for example, when a sucrose-6-acetate is being prepared, 1,3-diacetoxy-1,1,3,3-tetrabutyldistannoxane (distannoxane diacetate or DSDA) is most preferred.

When the organotin-based acylation promoter is a dinuclear species containing two atoms of tin per molecule (e.g. a distannoxane), preferably 0.5 to 2.5 molar equivalents, more preferably 0.75 to 1.2 molar equivalents, still more preferably 0.9 to 1.1 molar equivalents, and most preferably 1.0 molar equivalents of acylation promoter per mole of sucrose is present in the reaction mixture. When the organotin-based acylation promoter is a mononuclear species containing one atom of tin per molecule (e.g. a di(hydrocarbyl)tin oxide), preferably 0.5 to 2.5 molar equivalents, more preferably 0.8 to 1.5 molar equivalents, and most preferably 1.2 molar equivalents of acylation promoter per mole of sucrose is present in the reaction mixture.

To form the tin-sucrose adduct, a first reaction mixture comprising sucrose in a polar aprotic solvent is prepared by dissolving sucrose in the polar aprotic solvent, typically N,N-dimethyl formamide. Slight heating can be used to dissolve the sucrose. Then the organotin-based acylation promoter is added to the reaction mixture. Before the removal of water, which drives the reaction of sucrose with the promoter to form the tin-sucrose adduct, a base is also added to the reaction mixture. This may be done either before or after the organotin-based acylation promoter is added, as long as it is done before water is removed. Suitable bases include alkali metal carbonates, bicarbonates, hydroxides, tribasic phosphates, dibasic phosphates and carboxylates. Also suitable are amines, for example N,N-diisopropylethylamine (Hünig's base). Amines having a boiling point of at least 100° C. will typically be used, and more typically at least 120° C., although other boiling points are acceptable. Other tertiary amines may also be used, according to the invention, as well as primary and secondary amines. Suitable amines include, but are not limited to, methylamine, ethylamine, propylamine, isopropylamine, ethanolamine, aniline, tert-butylamine and morpholine, dimethylamine, diethylamine, diisopropylamine, piperidine, pyrrolidine, trimethylamine, triethylamine, pyridine, dimethylaminopyridine (DMAP), 1,8-diazabicyclo[5.4.0]undec-7-ene (DBU), and dimethylethanolamine (DMEA).

Water may then be removed from the resulting mixture by any convenient method. For example, an added non-polar co-solvent capable of removing water by co-distillation, such as described in Sankey, U.S. Pat. No. 5,470,969; White, EP 0 776 903; and Vernon, EP 0 475 619, the disclosures of which are incorporated herein by reference, may be used to facilitate efficient removal of the water of reaction. Such solvents are typically ones that do not react with the polar aprotic solvent, the organotin-based acylation promoter, or the sucrose; that produce a mixture with the polar aprotic solvent, the organotin-based acylation promoter, and the sucrose; that reflux with an internal reaction temperature within the range of from about 75° C. to about 153° C., preferably less than 100° C.; that co-distill with water; and that do not render the sucrose insoluble. Such solvents are typically those that are immiscible with water and form a constant-composition minimum-boiling azeotrope with water, such as saturated hydrocarbons, aromatic hydrocarbons, chlorinated hydrocarbons, ketones, and ethers. Examples of such solvents include cyclohexane, n-heptane, toluene, and isooctane (2,2,4-trimethylpentane). In one further aspect of the invention, the first reaction mixture, formed after removal of water and at least a portion of the polar aprotic solvent by distillation under reduced pressure, consists essentially of the sucrose, the polar aprotic solvent, the organotin-based acylation promoter, and their reaction products.

Preparation of Sucralose-6-Ester

To convert sucrose-6-ester to sucralose-6-ester, the hydroxyls at the 4, 1', and 6' positions of the sucrose-6-ester are converted to chloro groups, and the stereochemical configuration at the 4 position is inverted. Conversion of the hydroxyls in the 4, 1', and 6' positions of the ester to chloro groups with inversion of the stereochemical configuration at the 4 position is disclosed in Walkup, U.S. Pat. No. 4,980,463; Jai, U.S. Pat. Pub. 2006/0205936 A1; and Fry, U.S. Pat. Pub. 2007/0100139 A1; the disclosures of which are all incorporated herein by reference.

The chlorination process comprises the following steps. A reaction mixture is prepared comprising the sucrose-6-ester, a tertiary amide, and at least seven molar equivalents of a chlorination agent. For example, in one process, the sucrose-6-ester can be added in a feed stream that comprises about 20 wt % to about 40 wt % of the sucrose-6-ester. The ratio by weight of tertiary amide to total carbohydrate in the reaction mixture may be about 5:1 to about 12:1. Alternatively, a preformed chloroformiminium salt, such as (chloromethylene)dimethylammonium chloride (Arnold's reagent), can be used. (Chloromethylene)dimethylammonium chloride can be prepared, for example, by the reaction of phosgene with N,N-dimethyl formamide. Typically, the molar ratio of the (chloromethylene)dimethylammonium salt to the sucrose-6-ester is about 7:1 to about 11:1.

Subsequently, the hydroxyl groups of the sucrose-6-ester at the 2, 3, 4, 1', 3', 4', and 6' positions are converted to O-alkylformiminium groups. The resulting reaction mixture is heated at a temperature or temperatures and for a period of time or times sufficient to produce a product containing a derivative of sucralose-6-ester in which the remaining hydroxyl groups remain as O-alkylformiminium groups. For example, Walkup, U.S. Pat. No. 4,980,463, the disclosure of which is incorporated herein by reference, and Fry, U.S. 2007/0100139, the disclosure of which is incorporated herein by reference, disclose such processes.

Because formation of a chloroformiminium salt or Vilsmeier reagent is not essential to the chlorination reaction, chlorination agent refers to any compound that can be used to form a chloroformiminium salt or Vilsmeier reagent, or that can convert the hydroxyl groups of a sucrose-6-ester to chloro groups. Some chlorination agents that can be reacted with a tertiary amide to form a chloroformiminium salt include, for example, phosgene, phosphorus oxychloride, phosphorus pentachloride, thionyl chloride, sulfuryl chloride, oxalyl chloride, trichloromethyl chloroformate ("diphosgene"), bis (trichloromethyl) carbonate ("triphosgene"), and methanesulfonyl chloride. Tertiary amides that can be used include, for example, N,N-dimethyl formamide (DMF), N-formyl piperidine, N-formyl morpholine, and N,N-diethyl formamide. When N,N-dimethyl formamide is used as the tertiary amide, it can also be used as the reaction solvent. Co-solvents can be used at up to about 80 vol % or more of the liquid phase of the reaction medium. Useful co-solvents are those which are both chemically inert and which provide sufficient solvent power to enable the reaction to become essentially homogeneous at the monochlorination stage, for example toluene, o-xylene, 1,1,2-trichloroethane, 1,2-diethoxyethane, diethylene glycol dimethyl ether.

Quenching of the reaction mixture restores the hydroxyl groups at the 2, 3, 3', and 4' positions and forms the sucralose-6-ester. The reaction mixture can be quenched by the addition of about 0.5 to about 2.0 molar equivalents, typically about 1.0 to about 1.5 molar equivalents, of alkali relative to the amount of chlorination agent used in the reaction. An aqueous solution of an alkali metal hydroxide, such as sodium or potassium hydroxide; an aqueous slurry of an alkaline earth metal hydroxide, such as calcium hydroxide; or aqueous ammonium hydroxide can be used to quench the reaction. For example, an aqueous solution of an alkali metal hydroxide, such as aqueous sodium hydroxide, that contains about 5 wt % to about 35 wt %, typically about 8 wt % to about 20 wt %, and preferably about 10 wt % to about 12 wt % can be used.

As described below, quenching can be carried out by addition of alkali to the reaction mixture, by a dual stream process, or by a circulated process. In each case pH and temperature are controlled during addition of the alkali. Quenching is typically carried out at a pH between about 8.5 to about 10.5 and at a temperature of about 0° C. to about 60° C. Preferably, the pH should not be permitted to rise above about 10.5 during the course of the quenching reaction.

In the dual stream process, quenching is carried out by slow addition of the aqueous alkali with simultaneous slow addition of the chlorination reaction material into a reaction vessel. The chlorination reaction mixture and aqueous alkali are simultaneously added slowly until the desired quantity of chlorination reaction mixture has been added. Further aqueous alkali is added until the desired pH is reached. Then the temperature and pH are maintained at the desired levels for the remainder of the reaction. This process can be a batch or continuous process.

In the circulated process, quenching is carried out by circulating the chlorination reaction mixture from a vessel through a circulation loop. Chlorination reaction mixture and aqueous alkali are added slowly into this circulation loop. Sufficient aqueous alkali is added until the desired pH is reached. Then the temperature and pH are maintained at the desired levels for the remainder of the reaction. This process can be a batch or continuous process.

Following quenching, the reaction mixture can be neutralized by the addition of aqueous acid, for example aqueous hydrochloric acid. The resulting mixture comprises sucralose 6-ester, other carbohydrate including chlorinated carbohydrate impurities, unreacted tertiary amide, and salts in an aqueous solvent in which the predominant solvent is water.

Conversion of Sucralose-6-Ester to Sucralose

The sucralose 6-ester containing aqueous feed stream typically comprises both sucralose and sucralose-6-ester. Methods for hydrolyzing sucralose-6-ester are disclosed, for example in Catani, U.S. Pat. Nos. 5,977,349, 6,943,248, 6,998,480, and 7,049,435; Vernon, U.S. Pat. No. 6,890,581; El Kabbani, U.S. Pat. Nos. 6,809,198, and 6,646,121; Navia, U.S. Pat. Nos. 5,298,611 and 5,498,709, and U.S. Pat. Pub. 2004/0030124; Liesen, U.S. Pat. Pub. 2006/0188629 A1; Fry, U.S. Pat. Pub. 2006/0276639 A1; El Kabbani, U.S. Pat. Pub. 2007/0015916 A1; Deshpande, U.S. Pat. Pub. 2007/0160732 A1; and Ratnam, U.S. Pat. Pub. 2007/0270583 A1; the disclosures of which are all incorporated herein by reference.

For example, (a) sucralose-6-ester can be hydrolyzed to sucralose by raising the pH of the reaction mixture to about 11±1 at a temperature and for a time sufficient to effect removal of the protecting group, and (b) the tertiary amide is removed by, for example, stream stripping. Either step (a) or step (b) can be carried first. Alternatively, conversion of sucralose-6-ester to sucralose can be carried in methanol containing sodium methoxide. A trans-esterification reaction occurs that forms sucralose and the methyl ester of the acid, for example methyl acetate when the sucralose-6-ester is sucralose-6-acetate. The methyl ester of the acid can be removed by distillation, and the resulting sucralose containing product dissolved in water. The sucralose is eventually purified and isolated.

INDUSTRIAL APPLICABILITY

The process of the invention is useful in the preparation of sucralose. Sucralose is a high-intensity sweetener that can be used in many food and beverage applications, as well as in other applications. Such applications include, for example, beverages, combination sweeteners, consumer products, sweetener products, tablet cores (Luber, U.S. Pat. No. 6,277,409), pharmaceutical compositions (Luber, U.S. Pat. No. 6,258,381; Roche, U.S. Pat. No. 5,817,340; and McNally, U.S. Pat. No. 5,593,696), rapidly absorbed liquid compositions (Gelotte, U.S. Pat. No. 6,211,246), stable foam compositions (Gowan, Jr., U.S. Pat. No. 6,090,401), dental floss (Ochs, U.S. Pat. No. 6,080,481), rapidly disintegrating pharmaceutical dosage forms (Gowan, Jr., U.S. Pat. No. 5,876,759), beverage concentrates for medicinal purposes (Shah, U.S. Pat. No. 5,674,522), aqueous pharmaceutical suspensions (Ratnaraj, U.S. Pat. No. 5,658,919; Gowan, Jr. U.S. Pat. Nos. 5,621,005 and 5,374,659; and Blase, U.S. Pat. Nos. 5,409,907 and 5,272,137), fruit spreads (Antenucci, U.S. Pat. No. 5,397,588; and Sharp, U.S. Pat. No. 5,270,071), liquid concentrate compositions (Antenucci, U.S. Pat. No. 5,384,311), and stabilized sorbic acid solutions (Merciadez, U.S. Pat. No. 5,354,902). The determination of an acceptable sweetness can be accomplished by a variety of standard "taste test" protocols known in the art which are well known to those skilled in the art, such as, for example, the protocols referred to in Merkel, U.S. Pat. No. 6,998,144, and Shamil, U.S. Pat. No. 6,265,012.

The advantageous properties of this invention can be observed by reference to the following examples which illustrate but do not limit the invention.

EXAMPLES

A 300 mL three-neck round bottom Pyrex flask was fitted with a temperature probe connected to a temperature controller and a Dean-Stark trap topped with a condenser cooled by a circulating chiller at 10° C. Sucrose, 32.9 mmol (11.25 g) was added to the flask along with the indicated amount of base or other reagent (if any), and the Dean-Stark trap was filled with cyclohexane. Cyclohexane was also added to the reaction flask such that following the addition of the 1,3-diacetoxy-1,1,3,3-tetrabutyldistannoxane (DSDA) in cyclohexane solution the overall DMF to cyclohexane ratio in the reaction flask would be about 2.5:1. The addition of excess cyclohexane allowed for the DMF to cyclohexane ratio to be tightly controlled by slowly removing cyclohexane from the Dean-Stark trap until the desired reflux temperature of 95° C. was reached. To the cyclohexane and sugar mixture was added 94.4 g of DMF, followed by 32.9 mmol (19.73 g) DSDA in cyclohexane with a tin concentration around 50% w/w as measured via ICP (inductively coupled plasma atomic emission) spectroscopy. The temperature controller was set to 95° C. Cyclohexane was removed slowly from the Dean-Stark trap until the refluxing reaction mixture reached an internal temperature of 95° C. The reaction was refluxed at 95° C. for 90 min. The heat was removed and the reaction was allowed to cool. When the reaction temperature reached 40° C., 38.2 mmol (3.9 g, 1.16 eq.) of acetic anhydride was added and the reaction was allowed to stir for 2 hr. The reaction was quenched with 25 mL of water. The reaction mixture was extracted with 250 mL of cyclohexane to remove the regenerated tin compounds, leaving an aqueous solution of product that was analyzed by HPLC.

A reliable baseline (control) was established by running the above reaction ten times in the absence of added base, to obtain a statistically significant population of data for analysis of the base-spiked reactions. The reaction was repeated with the inclusion of a reagent (a base, or in some cases a non-basic sodium salt), which was added to the reaction flask at the same time that the sucrose was added at the beginning of the reaction setup. Reactions were run with each of the indicated reagents several times and the data were averaged. Results of the baseline and reagent-containing reactions are shown in Tables 1 and 2.

Molar Yield Increase

Table 1 presents the data from the experiments in terms of deviation from the baseline composition. The species labeled Di1-Di4 are sucrose diacetates; Tri1 and Tri2 are sucrose triacetates; and S-6-A, S-4-A and S-2-A are sucrose-6-acetate, sucrose-4-acetate and sucrose-2-acetate respectively; and Mono1 and Mono2 are sucrose monoacetates other than S-6-A, S-4-A and S-2-A. The equivalents are reported relative to the amount of acylating agent (acetic anhydride).

TABLE 1

| | Molar yield deviation from baseline | | | | | | | | | | | | | |
|---|---|---|---|---|---|---|---|---|---|---|---|---|---|---|
| SampleName | Unk. | Di1 | Di2 | Di3 | Di4 | Mono1 | Mono2 | S-4-A | S-2-A | S-6-A | Tri1 | Tri2 | Sucrose | Total |
| Average Baseline | 0.31 | 4.28 | 8.34 | 1.06 | 3.34 | 0.00 | 1.83 | 0.35 | 5.28 | 61.76 | 0.60 | 0.07 | 3.82 | 91.03 |
| Sodium carbonate 1.0 eq. | −0.31 | 1.34 | −3.20 | 2.49 | −2.04 | 0.00 | 1.69 | 2.42 | −2.35 | −3.53 | −0.60 | −0.07 | 11.26 | 7.10 |
| Sodium carbonate 0.5 eq. | −0.31 | 3.06 | −1.62 | 2.28 | −2.23 | 0.00 | 2.05 | 2.24 | −1.24 | −4.84 | −0.60 | −0.07 | 6.72 | 5.44 |
| Sodium carbonate 0.25 eq. | −0.31 | 1.34 | −0.66 | 2.32 | −2.59 | 0.09 | −0.27 | 0.50 | −2.02 | 8.50 | −0.32 | −0.05 | 0.44 | 6.98 |
| Sodium carbonate 0.1 eq. | −0.26 | 1.15 | −1.20 | 1.49 | −2.47 | 0.23 | −0.23 | 0.27 | −1.69 | 8.35 | 0.22 | −0.07 | −1.01 | 4.78 |
| Sodium carbonate 0.05 eq. | −0.19 | 0.38 | −0.54 | 1.05 | −1.75 | 0.14 | −0.61 | 0.12 | −1.83 | 8.25 | 0.00 | −0.05 | −2.30 | 2.66 |

TABLE 1-continued

Molar yield deviation from baseline

| SampleName | Unk. | Di1 | Di2 | Di3 | Di4 | Mono1 | Mono2 | S-4-A | S-2-A | S-6-A | Tri1 | Tri2 | Sucrose | Total |
|---|---|---|---|---|---|---|---|---|---|---|---|---|---|---|
| Sodium carbonate 0.01 eq. | −0.06 | 0.11 | −0.05 | 0.15 | −0.33 | 0.00 | −0.22 | 0.04 | −0.80 | 5.25 | 0.18 | −0.07 | −1.34 | 2.85 |
| Potassium carbonate 0.1 eq. | −0.23 | 0.82 | −0.42 | 0.97 | −2.22 | 0.00 | −0.70 | 0.20 | −2.81 | 10.27 | −0.04 | −0.07 | −2.24 | 3.53 |
| Sodium hydroxide (23%) 0.2 eq. | −0.25 | 0.41 | −1.24 | 1.34 | −2.32 | 0.18 | −0.57 | 0.89 | −2.21 | 11.74 | −0.17 | −0.07 | −0.85 | 6.87 |
| Sodium acetate 0.2 eq. | −0.26 | 1.27 | −0.71 | 1.36 | −2.38 | 0.15 | −0.31 | 0.17 | −2.23 | 6.58 | 0.11 | −0.07 | −1.32 | 2.37 |
| Sodium phosphate dibasic 0.1 eq. | −0.07 | 0.23 | −0.29 | 0.39 | −0.79 | 0.00 | −0.32 | 0.14 | −1.13 | 4.80 | 0.12 | −0.01 | −1.84 | 1.23 |
| Sodium hydrogen sulfate 0.1 eq. | 0.56 | −0.52 | −0.09 | −0.09 | 0.35 | 0.00 | −0.21 | 0.00 | −0.02 | −4.54 | 0.12 | 0.19 | 0.64 | −3.61 |
| Sodium sulfate 0.1 eq. | 0.25 | −0.22 | 1.33 | −0.07 | 0.23 | 0.00 | −0.48 | −0.02 | −0.96 | −1.21 | 0.13 | 0.16 | −0.70 | −1.55 |

The above data clearly illustrate the advantages of including base in the mixture of sucrose and tin compound prior to the dehydration step. At higher levels (0.5-1 eq.), sodium carbonate causes yield loss, but at lower levels the yield is increased over baseline for all conditions tested. Furthermore, addition of an aqueous sodium hydroxide solution also affords a significant yield increase. This is particularly surprising, given that the type of intermediates involved in dehydration are sensitive to water. Potassium carbonate also gives a significantly beneficial effect; at 0.1 eq. the S-6-A yield increase of 10.3 percentage points is greater than the increase for the corresponding level of sodium carbonate, 8.4 percentage points. Without wishing to be bound by any particular theory or explanation, the inventors believe that this difference may possibly be attributed to the increased solubility of potassium carbonate in the dimethyl formamide solvent. The non-basic sodium sulfate and hydrogen sulfate had no beneficial effect, and in fact hurt yield somewhat.

From the above data, it is clear that the best result is achieved through addition of 0.2 molar equivalents of sodium hydroxide (23 wt. % aqueous); this base increased the molar yield of S-6-A by 11.7 percentage points.

Note that even with a very small base addition, a beneficial effect on S-6-A yield is still observed. The reason for this surprising effect is not clear, but the effect is significant.

Selectivity Increase

Table 2 presents the data in terms of selectivity. Each sample is normalized to 100% such that the preference for particular species can be seen.

An increase in reaction selectivity is observed over the baseline conditions for all bases, with the exception of the higher level sodium carbonate addition experiments (0.5 and 1.0 eq.). For example, note the lower amounts of Di4, S-2-A and unreacted sucrose. For these reactions, the elevated sucrose levels suggest incomplete reaction or product degradation; in either case, this may in at least some cases indicate an upper limit on the level of sodium carbonate one can add and still receive benefit.

With decreasing sodium carbonate levels of 0.25, 0.1 and 0.05 eq., there is a slight increase in selectivity, which begins to drop off at 0.01 eq., the lowest level tried. Again, the potassium carbonate gives a slightly better result than the equivalent sodium carbonate addition, again attributed to increased solubility allowing greater manifestation of the beneficial effect. Sodium hydroxide increased the selectivity of the acetylation reaction by a considerable 7.2 percentage points, again surprising in that it was added as an aqueous solution to a mixture that ultimately was dehydrated.

It is notable that the best results were obtained at base levels that were significantly lower than a stoichiometric amount based on the acylating agent (or the DSDA or sucrose).

Further acetylations were performed using 0.2 eq. of Hünig's base (a tertiary amine; N,N-diisopropylethylamine) to investigate whether organic bases might also improve acetylation. As before, the base was added prior to dehydration. Table 3 summarizes the results, compared against the average baseline, NaOH and sodium carbonate runs reported above. As can be seen, Hünig's base also significantly improved S-6-A yield. Other tertiary amines may also be used, according to the invention, as well as primary and secondary amines. Data for tert-butylamine and morpholine (primary and secondary amines, respectively) are also shown, and also improved yield of S-6-A. Other suitable amines include, but are not limited to, methylamine, ethylamine, propylamine, isopropylamine, ethanolamine, aniline, dimethylamine, diethylamine, diisopropylamine, piperidine, pyrrolidine, trimethylamine, triethylamine, pyridine, dimethylaminopyridine (DMAP), DBU, dimethylethanolamine (DMEA).

TABLE 2

Acetylation normalized yields compared to baseline

| SampleName | Unk. | Di1 | Di2 | Di3 | Di4 | Mono1 | Mono2 | S-4-A | S-2-A | S-6-A | Tri1 | Tri2 | Sucrose | Total |
|---|---|---|---|---|---|---|---|---|---|---|---|---|---|---|
| Average Baseline | 0.34 | 4.71 | 9.16 | 1.17 | 3.67 | 0.00 | 2.01 | 0.38 | 5.80 | 67.84 | 0.65 | 0.07 | 4.19 | 100.00 |
| Sodium carbonate 1.0 eq. | 0.00 | 5.73 | 5.24 | 3.62 | 1.32 | 0.00 | 3.58 | 2.82 | 2.99 | 59.34 | 0.00 | 0.00 | 15.36 | 100.00 |
| Sodium carbonate 0.5 eq. | 0.00 | 7.61 | 6.96 | 3.47 | 1.15 | 0.00 | 4.02 | 2.68 | 4.19 | 59.00 | 0.00 | 0.00 | 10.92 | 100.00 |
| Sodium carbonate 0.25 eq. | 0.00 | 5.74 | 7.84 | 3.45 | 0.76 | 0.09 | 1.59 | 0.87 | 3.33 | 71.68 | 0.28 | 0.02 | 4.35 | 100.00 |
| Sodium carbonate 0.1 eq. | 0.05 | 5.67 | 7.45 | 2.66 | 0.91 | 0.24 | 1.67 | 0.65 | 3.75 | 73.17 | 0.85 | 0.00 | 2.94 | 100.00 |
| Sodium carbonate 0.05 eq. | 0.12 | 4.98 | 8.33 | 2.25 | 1.70 | 0.15 | 1.30 | 0.50 | 3.68 | 74.72 | 0.64 | 0.01 | 1.61 | 100.00 |
| Sodium carbonate 0.01 eq. | 0.26 | 4.68 | 8.83 | 1.29 | 3.21 | 0.00 | 1.71 | 0.41 | 4.78 | 71.38 | 0.82 | 0.00 | 2.64 | 100.00 |
| Potassium carbonate 0.1 eq. | 0.08 | 5.40 | 8.38 | 2.14 | 1.19 | 0.00 | 1.19 | 0.58 | 2.61 | 76.17 | 0.59 | 0.00 | 1.67 | 100.00 |
| Sodium hydroxide (23%) 0.2 eq. | 0.06 | 4.80 | 7.25 | 2.45 | 1.04 | 0.19 | 1.28 | 1.27 | 3.14 | 75.07 | 0.43 | 0.00 | 3.03 | 100.00 |
| Sodium acetate 0.2 eq. | 0.05 | 5.94 | 8.17 | 2.60 | 1.02 | 0.16 | 1.62 | 0.56 | 3.27 | 73.16 | 0.76 | 0.00 | 2.67 | 100.00 |
| Sodium phosphate dibasic 0.1 eq. | 0.25 | 5.34 | 9.52 | 1.71 | 3.01 | 0.00 | 1.61 | 0.51 | 4.43 | 70.91 | 0.76 | 0.13 | 1.87 | 100.00 |
| Sodium hydrogen sulfate 0.1 eq. | 0.98 | 4.71 | 10.31 | 1.22 | 4.62 | 0.00 | 1.82 | 0.39 | 5.93 | 64.46 | 0.81 | 0.28 | 4.47 | 100.00 |
| Sodium sulfate 0.1 eq. | 0.61 | 4.95 | 11.78 | 1.21 | 4.35 | 0.00 | 1.48 | 0.36 | 4.75 | 66.44 | 0.80 | 0.24 | 3.05 | 100.00 |

Also included in Table 3 are data obtained by adding 0.2 eq. of NaOH (23% aqueous) after dehydration, rather than with the sucrose. Rather than improving the yield, addition of NaOH at this point in the process was strongly detrimental.

TABLE 3

|  | S-6-A yield, % | Difference from baseline yield, % |
|---|---|---|
| Average baseline | 61.76 | 0.00 |
| NaOH (23%) 0.2 Eq. | 73.49 | 11.73 |
| NaOH post-dehydration | 31.41 | −30.35 |
| Sodium Carbonate 0.1 Eq. | 70.11 | 8.35 |
| Hünig's base 0.2 Eq. | 64.61 | 2.85 |
| tert-Butylamine 0.2 Eq. | 70.84 | 9.08 |
| Morpholine 0.2 Eq. | 63.13 | 1.37 |

Although the invention is illustrated and described herein with reference to specific embodiments, the invention is not intended to be limited to the details shown. Rather, various modifications may be made in the details within the scope and range of equivalents of the claims without departing from the invention.

What is claimed is:

1. A method of forming a sucrose-6-ester, comprising in sequence the steps of:
   a) contacting sucrose with an organotin-based acylation promoter selected from 1,3-diacyloxy-1,1,3,3-tetra-(hydrocarbyl)distannoxanes in a solvent in the presence of a base selected from the group consisting of sodium carbonate, potassium carbonate, sodium hydroxide, sodium acetate and sodium phosphate dibasic;
   b) removing water of reaction to form a tin-sucrose adduct; and
   c) contacting the tin-sucrose adduct with an acylating agent to form the sucrose-6-ester;
   wherein the base is present in a range from 0.01 to 0.25 equivalents relative to the acylating agent.

2. The method of claim 1, wherein the base is present at a level in a range from 0.05 to 0.25 equivalents relative to the acylating agent.

3. The method of claim 1, wherein the base comprises sodium carbonate or potassium carbonate.

4. The method of claim 1, wherein the base comprises sodium acetate.

5. The method of claim 1, wherein the base comprises sodium phosphate dibasic.

6. The method of claim 1, wherein the base is present at a level in a range from 0.025 to 0.25 equivalents relative to the acylating agent.

7. The method of claim 1, wherein the base is present at a level in a range from 0.05 to 25 equivalents relative to the acylating agent.

8. The method of claim 1, wherein the organotin-based acylation promoter comprises 1,3-diacetoxy-1,1,3,3-tetrabutyldistannoxane.

9. The method of claim 1, wherein the organotin-based acylation promoter comprises 1,3-dibenzoyloxy-1,1,3,3-tetrabutyldistannoxane.

10. The method of claim 1, wherein the acylating agent comprises an acyl anhydride.

11. The method of claim 1, wherein the acylating agent comprises acetic anhydride.

12. The method of claim 1, wherein the acylating agent comprises benzoic anhydride.

13. The method of claim 1, wherein the solvent comprises a tertiary amide.

14. The method of claim 13, wherein the tertiary amide comprises dimethyl formamide.

15. The method of claim 1, wherein the solvent further comprises a solvent capable of forming an azeotrope with water.

16. The method of claim 15, wherein the solvent capable of forming an azeotrope with water comprises a hydrocarbon solvent.

17. A method of making sucralose, comprising in sequence the steps of:
   a) contacting sucrose with an organotin-based acylation promoter selected from 1,3-diacyloxy-1,1,3,3-tetra-(hydrocarbyl)distannoxanes in a solvent in the presence of a base selected from the group consisting of sodium carbonate, potassium carbonate, sodium hydroxide, sodium acetate and sodium phosphate dibasic;
   b) removing water of reaction to form a tin-sucrose adduct;
   c) contacting the tin-sucrose adduct with an acylating agent to form a sucrose-6-ester; and
   d) converting the sucrose-6-ester to sucralose and isolating and purifying the sucralose;
   wherein the base is present in a range from 0.01 to 0.25 equivalents relative to the acylating agent.

* * * * *

UNITED STATES PATENT AND TRADEMARK OFFICE
CERTIFICATE OF CORRECTION

PATENT NO. : 8,927,706 B2
APPLICATION NO. : 13/262102
DATED : January 6, 2015
INVENTOR(S) : Thomas Kennedy Hutton It is certified that error appears in the above-identified patent and that said Letters Patent is hereby corrected as shown below:

In the Claims

Claim 2, Column 11, line 40, "2. The method of claim 1, wherein the base is present at a level in a range from 0.05 to 0.25 equivalents relative to the acylating agent." should read --2. The method of claim 1, wherein the base comprises sodium hydroxide.--

Claim 7, Column 12, line 6, "7. The method of claim 1, wherein the base is present at a level in a range from 0.05 to 25 equivalents relative to the acylating agent." should read --7. The method of claim 1, wherein the base is present at a level in a range from 0.05 to 0.25 equivalents relative to the acylating agent.--

Signed and Sealed this
Fourteenth Day of April, 2015

Michelle K. Lee
*Director of the United States Patent and Trademark Office*